United States Patent
Salman et al.

(10) Patent No.: US 6,900,296 B2
(45) Date of Patent: May 31, 2005

(54) COST EFFECTIVE METHOD FOR SELECTIVE METHYLATION OF ERYTHROMYCIN A DERIVATIVES

(75) Inventors: Mohammad Salman, Haryana (IN); Parma Chandra Ray, New Delhi (IN); Kiran Kumar Gangakhedkar, Haryana (IN); Harish Niranjan Lal Dorwal, Haryana (IN); Naresh Kumar, Haryana (IN)

(73) Assignee: Ranbaxy Laboratories Limited, New Delhi (IN)

( * ) Notice: Subject to any disclaimer, the term of this patent is extended or adjusted under 35 U.S.C. 154(b) by 130 days.

(21) Appl. No.: 10/276,505

(22) PCT Filed: May 7, 2001

(86) PCT No.: PCT/IB01/00770
§ 371 (c)(1),
(2), (4) Date: Jul. 3, 2003

(87) PCT Pub. No.: WO01/87807
PCT Pub. Date: Nov. 22, 2001

(65) Prior Publication Data
US 2004/0010128 A1 Jan. 15, 2004

(30) Foreign Application Priority Data
May 15, 2000 (IN) .................................. 515/DEL/2000

(51) Int. Cl.$^7$ .................................................. C07H 1/00
(52) U.S. Cl. ....................... 536/7.2; 536/18.5; 536/18.6
(58) Field of Search ................................. 536/7.2, 18.5, 536/18.6

(56) References Cited

U.S. PATENT DOCUMENTS

| | | | |
|---|---|---|---|
| 4,331,803 A | 5/1982 | Watanabe et al. | 536/7.2 |
| 4,670,549 A | 6/1987 | Morimoto et al. | 536/7.4 |
| 4,672,109 A | 6/1987 | Watanabe et al. | 536/7.2 |

*Primary Examiner*—Elli Peselev
(74) *Attorney, Agent, or Firm*—Jayadeep R. Desmukh, Esq.; George E. Heibel, Esq.; William D. Hare, Esq.

(57) ABSTRACT

The invention relates to a cost effective and industrially advantageous process for the selective methylation of a hydroxy group at the 6 position of erythromycin A derivative which comprised methylating the erythromycin A derivative with a methylating agent in a mixture of toluene and a ploar aprotic solvent.

11 Claims, No Drawings

COST EFFECTIVE METHOD FOR SELECTIVE METHYLATION OF ERYTHROMYCIN A DERIVATIVES

This application is a 371 of PCT/IB01/00770 filed May 7, 2001.

FIELD OF THE INVENTION

The present invention relates to a cost effective and industrially advantageous process for the selective methylation of a hydroxy group at the 6 position of erythromycin A derivatives.

BACKGROUND OF THE INVENTION

6-O-Methylerythromycin A (Clarithromycin) of Formula I,

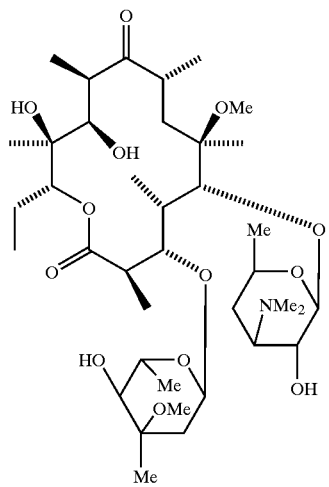

FORMULA I is a second-generation semi-synthetic macrolide antibiotic and exhibits excellent antibacterial activity against gram-positive bacteria, some gram-negative bacteria, anaerobic bacteria, mycoplasma, and chlamydia. Furthermore, it has greater stability at physiological pH, which renders it as a superior alternative to its parent compound, erythromycin. Clarithromycin is a useful therapy for infections of the upper and lower respiratory tract, for infections due to chlamydia, mycoplasma and legionella, for infections of soft tissue, and for the eradication of *H. Pylori* (when used in combination with acid suppressing agents).

The critical step in the synthesis of clarithromycin is the selective methylation of 6-hydroxy position of erythromycin A of Formula II,

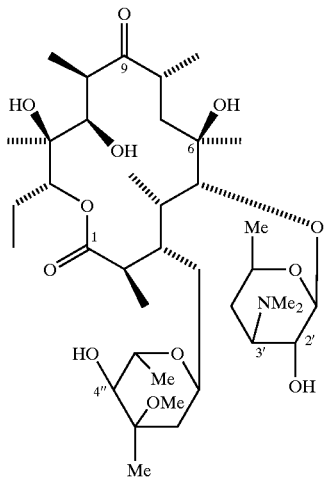

FORMULA II since erythromycin A has many hydroxy groups. In U.S. Pat. No. 4,331,803, there is described a method for methylating the hydroxy group at the 6-position of erythromycin A derivatives, with a methylating agent in the presence of a base in a polar solvent. By following this method one gets compounds which are methylated at hydroxy groups other than the 6-position along with the 6-0-methyl form and therefore, requires a good purification technique to get the intended 6-0-methyl form which reduces the yield drastically.

Another method described in U.S. Pat. No. 4,672,109 for carrying out the selective methylation recommends use of a polar aprotic solvent such as dimethyl sulphoxide (DMSO), N, N-dimethylformamide (DMF), hexamethylphosphoric triamide, a mixture consisting of two or more of these solvents, or a mixture consisting of one of these solvents and tetrahydrofuran. The most preferred example of the solvents in the prior art is the mixture of DMSO and tetrahydrofuran for affecting the desired methylation followed by quenching with aqueous dimethylamine solution and extraction with hexanes.

A major limitation of the above procedure from a commercial view point, is that recovery of tetrahydrofuran which becomes extremely difficult to accomplish as it distributes almost equally, among both the aqueous dimethylsulphoxide and hexane layers and forms a constant boiling azeotrope with hexanes. Tetrahydrofuran is an expensive solvent and adds a significant cost factor in the overall cost of production of clarithromycin. Hence, non-accomplishment of the recovery of tetrahydrofuran makes the said process costly and renders it unattractive on a commercial scale. Moreover, the use of solvent tetrahydrofuran is burdened with the risk of fire and explosion.

SUMMARY OF THE INVENTION

It is an object of the present invention to develop an alternate commercially viable solvent system, which does not use tetrahydrofuran for carrying out selective methylation of erythromycin A derivatives and would be easy to separate and recover at commercial scale.

The present invention relates to a process for carrying out selective methylation at 6-position of erythromycin A derivatives in which the term "erythromycin A derivative" means erythromycin A having no substituent group or having conventional substituent groups in organic synthesis, in place of a hydrogen atom of the 2' and 4" hydroxy groups and/or a methyl group of the 3'-dimethyl amino group which is prepared according to the conventional manner. Erythromycin A derivatives also include 2',4"-bis trimethyl silyl or as 2'-carbobenzyloxy or as 3'-dicarbobenzyloxy) erythromycin A derivatives. Further the term erythromycin A derivatives also include "erythromycin A 9 oximes" having at the 9-position the general formula,

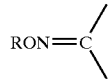

wherein R is a hydrogen atom or a substituent group such as lower alkyl group, which is substituted, or unsubstituted, an aryl substituted methyl group, a substituted oxyalkyl group or a thioalkyl group.

More particularly, the present invention relates to a process, which comprises dissolving erythromycin, A derivative in a mixture of toluene and a polar aprotic solvent and reacting it with a methylating agent in the presence of a base.

The above reaction of methylation is affected in a mixture of toluene and a dipolar aprotic solvent, preferred examples of the polar aprotic solvents used are dimethyl sulphoxide, N,N-dimethylformamide, hexamethyl phosphoric triamide and the like. The ratio of toluene and dipolar aprotic solvent varies from 1:1 to 1:5, preferably 1:1.

Examples of the methylating agents are methyl halides such as methyl iodide, methyl bromide and the like; dimethyl sulphate, methyl p-tolune sulphonate, methyl methane sulphonate and the like.

The suitable base is selected from the group consisting of potassium hydroxide, sodium hydroxide, sodium hydride, potassium hydride and the like.

Generally the reaction can be carried out at a temperature up to 100° C., preferably at 5–25° C., more preferably at 5–15° C. However, carrying out the methylation reaction at higher temperature leads to the formation of undesired products and therefore, requires extra purification to get the pure 6-O-methyl form which reduces the yield.

The above reaction is efficiently accomplished in 1–2 hours. However, the length of time required will vary depending upon such factors as temperature of reaction, concentration and presence or absence of efficient stirring.

After the reaction is over the reaction mixture is quenched in aqueous dimethylamine solution and more water is added. Toluene layer is separated and subjected to vacuum distillation to recover pure toluene as a recovered solvent and desired methylated compound.

In the following section preferred embodiments are described by way of examples to illustrate the process of this invention. However, this is not intended in any way to limit the scope of the present invention.

DETAILED DESCRIPTION OF THE INVENTION

EXAMPLE 1

Preparation of 6-O-Methyl-2'-O-benzyloxy-carbonyl Erythromycin A 9-[O-(1-methoxy-1-methylethyl) oxime.

2'-O-Benzyloxycarbonyl erythromycin A 9-[O-(1-methoxy-1-methylethyl) oxime] (125 g, 0.131 moles) was dissolved into a mixture of toluene (1875 ml) and dimethylsulphoxide (1875 ml) at 20–25° C. under stirring. Cooled the reaction mixture to about 10° C., added dimethylsulphate (24.7 gm, 0.196 moles) and potassium hydroxide (12.96 gm, 0.196 moles) at this temperature under stirring. Stirred at this temperature for about 2 hours. After the completion of the reaction, the reaction mixture was diluted with water and layers were separated. Aqueous layer was again extracted with toluene (2×250 ml) and the combined toluene layer was washed with water. The solvent was recovered from the toluene layer through distillation under reduce pressure to give 121 gm of crude 6-0-methyl-2'-benzyloxy carbonyl erythromycin A9-[O-(1-methoxy-methylethyl)oxime] which on crystallization gave 84 gm (yield 65% of theory) of pure product. Recovery of toluene was 2257 ml, (95% v/v) and purity by GC, 99.5%.

EXAMPLE 2

Preparation of 6-O-Methyl-2'-O,3'-N-bis (benzyloxycarbonyl)-N-demethyl Erythromycin A 9-[0-(1-methoxy-1-methylethyl) oxime]

Dissolved 2'-O,3'-N-bis(benzyloxycarbonyl)-N-demethylerythromycin A 9-[O-(1-methoxy-1-methylethyl) oxime] (5 gm, 0.0051 mole) in a mixture of toluene (75 ml) and DMSO (75 ml) at 20–25° C. under stirring. Cooled it to 10° C., added methyl iodide (0.79 gm, 0.0055 moles) and potassium hydroxide (0.37 gm, 0.0055 moles). Stirred the reaction mixture for about 1 hr. After the reaction was over, the reaction mixture was quenched with aqueous dimethylamine solution (40% w/v), added water to it, stirred and layers were separated. Extracted the aqueous layer with toluene (2×10 ml) and toluene was recovered (87 ml, 92% v/v purity by GC>99%) from the combined toluene layer under vacuum to give 4.29 gm of crude 6-O-methyl-2'-O,3'-N-bis(benzyloxycarbonyl)-N-demethyl erythromycin A9-[O-(1-methoxy-1-methylethyl)oxime] which on crystallization gave 3.56 gm (yield 70%).

EXAMPLE 3

Preparation of 2',4"-O-Bis (trimethylsilyl)-6-O-methylerythromycin A 9-[O-(1-methoxy-1-methylethyl)oxime]

2',4"-O-(trimethylsilyl) A9-[O-(1-methoxy-1-methylethyl)oxime](50 gm, 0.052 moles) was dissolved in toluene (750 ml) at 25–30° C. To it was added dimethyl sulphoxide (750 ml) and the resulting reaction mixture was cooled to 5–8° C. Added dimethyl sulphate (7.19 gm, 0.057 moles) and potassium hydroxide (3.76 gm, 0.057 moles) at 5–8° C. Stirred the reaction mixture for about 2 hours at 5–8° C. and added excess of dimethylamine aqueous solution (40% w/v). Water (500 ml) was added to the reaction mixture, separated the toluene layer and extracted the aqueous layer with toluene (2×250 ml). The combined toluene layer was washed with water (2×100 ml) and concentrated to give the desired methylated crude product (48.2 gm) which on crystallization gave 35.5 gm of pure product. Toluene recovery was (1180 ml 94.5% v/v; purity by GC .99.5°/ ).

EXAMPLE 4

Preparation of 2',4"-O-Bis (trimethylsilyl)-6-O-methylerythromycin A 9-[O-(1-methoxy-1-methylethyl)oxime]

2',4"-O-Bis (trimethylsilyl) erythromycin A9-[O-(1-methoxy-1-methylethyl)oxime] (50 gm, 0.052 moles) was dissolved in toluene (750 ml) at 25–30° C. and added DMSO (750 ml) to it. The reaction mixture was then cooled to 8–12° C. To it was added methyl iodide (8.08 gm, 0.057 moles) and potassium hydroxide (3.76 gm, 0.057 moles) at 8–12° C. Stirred the resulting reaction mixture for about 2 hours at the same temperature. After the reaction was over, added excess of aqueous dimethylamine solution(40% w/v) and water (500 ml) keeping the temperature at 8–12° C. The aqueous layer was further extracted with toluene (2×250ml). The combined toluene layer was subjected to vacuum distillation to recover toluene completely to give the crude methylated product (48.4 gm) which after crystallization gave 35.7 gm (70% yield) of pure product. Toluene recovery was (1137 ml, 91% v/v) purity by GC (>99%).

While the present invention has been described in terms of its specific embodiments, certain modifications and equivalents will be apparent to those skilled in the art and are intended to be included within the scope of the present invention.

We claim:

1. A process for selective methylation of a hydroxy group at the 6-position of an erythromycin A derivative which comprises methylating the erythromycin A derivative with a methylating agent in a mixture of toluene and a polar aprotic solvent in the presence of a base, wherein the erythromycin A derivative is an erythromycin A having no substituent group or having substituent groups in place of (1) hydrogen atom(s) of the 2' and/or 4" hydroxy groups or (2) one or both methyl groups of the 3'-dimethylamino group or (3) hydrogen atom(s) of the 2' and/or 4" hydroxy groups, and a methyl group of 3'-dimethylamino group, wherein the substituent group is selected from the group consisting of trimethylsilyl or carbobenzyloxy.

2. The process according to claim 1, wherein the methylating agent is methyl iodide, methyl bromide, methyl chloride, dimethyl sulphate, methyl p-toluene sulphonate or methyl methanesulphonate.

3. The process according to claim 1, wherein the polar aprotic solvent is selected from the group consisting of dimethyl sulphoxide, N,N-dimethyl formamide and hexamethyl phosphoric triamide.

4. The process according to claim 3, wherein the polar aprotic solvent is dimethyl sulphoxide.

5. The process according to claim 1, wherein the base is potassium hydroxide, sodium hydroxide, sodium hydride or potassium hydride.

6. The process according to claim 1, wherein 1.0 to 2.0 molar equivalent of the base is used per mole of the erythromycin A derivative.

7. The process according to claim 1, wherein methylation is carried out in a mixture of toluene and polar aprotic solvent present in the ratio ranging from 1:1 to 1:5.

8. The process according to claim 7, wherein the ratio of toluene and polar aprotic solvent is 1:1.

9. The process according to claim 1, wherein the reaction is carried out at a temperature ranging from 5–100° C.

10. The process according to claim 9, wherein the reaction is carried out at a temperature 5–15° C.

11. The process according to claim 1, wherein the erythromycin A derivative is an erythromycin A 9 oxime at 9-position of the general formula,

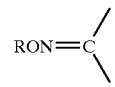

wherein R is a hydrogen atom or a substituent group selected from the group consisting of substituted or unsubstituted lower alkyl group, aryl substituted methyl group, substituted oxyalkyl group, or a thioalkyl group.

* * * * *

UNITED STATES PATENT AND TRADEMARK OFFICE
CERTIFICATE OF CORRECTION

PATENT NO. : 6,900,296 B2
DATED : May 31, 2005
INVENTOR(S) : Salman et al.

It is certified that error appears in the above-identified patent and that said Letters Patent is hereby corrected as shown below:

Title page,
Item [75], Inventors, "Parma" should read -- Purna --.
Item [57], ABSTRACT,
Line 4, "comprised" should read -- comprises --.
Line 5, "ploar" should read -- polar --.

Column 2,
Line 13, replace formula II with:

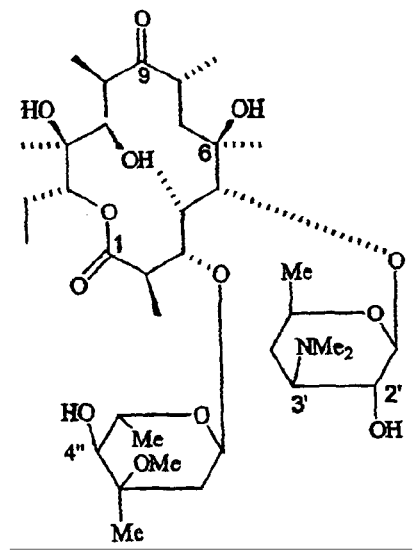

Column 3,
Line 4, "-dicarbobenzyloxy)" should read -- -dicarbobenzyloxy --.
Line 61, "oxime." should read -- oxime] --.

Column 4,
Line 9, "6-0-" should read -- 6-O- --.
Lines 10, 33, 43 and 65, "A9" should read -- A 9 --.
Lines 17, 20 and 32 "-O,3'-" should read -- -O, 3'- --.

UNITED STATES PATENT AND TRADEMARK OFFICE
CERTIFICATE OF CORRECTION

PATENT NO. : 6,900,296 B2
DATED : May 31, 2005
INVENTOR(S) : Salman et al.

It is certified that error appears in the above-identified patent and that said Letters Patent is hereby corrected as shown below:

Column 4 (cont'd),
Line 19, "9-[0" should read -- 9-[O --.

Signed and Sealed this

Twenty-fifth Day of October, 2005

JON W. DUDAS
*Director of the United States Patent and Trademark Office*